US008715570B2

(12) United States Patent
Lindblad et al.

(10) Patent No.: US 8,715,570 B2
(45) Date of Patent: May 6, 2014

(54) DEVICE AND A METHOD FOR STERILIZATION OF PACKAGES (75) Inventors: Ulf Lindblad, Lund (SE); Jenny Olsson, Bjärred (SE)

(73) Assignee: Tetra Laval Holdings & Finance S.A., Pully (CH)

( * ) Notice: Subject to any disclaimer, the term of this patent is extended or adjusted under 35 U.S.C. 154(b) by 111 days.

(21) Appl. No.: 13/377,980

(22) PCT Filed: Jun. 24, 2010

(86) PCT No.: PCT/SE2010/000177
§ 371 (c)(1),
(2), (4) Date: Dec. 13, 2011

(87) PCT Pub. No.: WO2011/002380
PCT Pub. Date: Jan. 6, 2011

(65) Prior Publication Data
US 2012/0087829 A1 Apr. 12, 2012

(30) Foreign Application Priority Data
Jul. 3, 2009 (SE) ..................................... 0900907

(51) Int. Cl.
*A61L 2/08* (2006.01)
*A61L 9/00* (2006.01)
*A61L 2/00* (2006.01)
*A61L 12/00* (2006.01)
A61L 2/20 (2006.01)
A61L 9/015 (2006.01)
A01N 1/02 (2006.01)

(52) U.S. Cl.
CPC .. *A61L 12/00* (2013.01); *A61L 2/00* (2013.01); *A61L 2/202* (2013.01); *A61L 2/208* (2013.01); *A61L 9/015* (2013.01); *A01N 1/0215* (2013.01); *A61L 8/22* (2013.01)
USPC ........ 422/28; 422/1; 422/26; 422/32; 422/33; 422/295; 422/297; 422/298; 422/300; 422/305; 422/307

(58) Field of Classification Search
CPC ........ A01N 1/0215; A61L 12/00; A61L 2/00; A61L 2/202; A61L 2/208; A61L 9/015; A61K 8/22

USPC .............. 422/1, 26, 28, 30, 32–33, 295, 422/297–298, 300, 305, 307
See application file for complete search history.

(56) References Cited

U.S. PATENT DOCUMENTS

| 6,431,227 | B1 | 8/2002 | Ter Haar | |
|---|---|---|---|---|
| 2001/0000558 | A1* | 5/2001 | Taggart | ........................ 53/138.1 |
| 2008/0181826 | A1 | 7/2008 | Windsheimer | |

FOREIGN PATENT DOCUMENTS

| DE | 3931672 A1 | 4/1991 |
|---|---|---|
| EP | 0 597 097 A1 | 5/1994 |
| WO | WO 02/051450 A1 | 7/2002 |
| WO | WO 2004/054883 A1 | 7/2004 |
| WO | WO 2007/024173 A1 | 3/2007 |

OTHER PUBLICATIONS

International Search Report (PCT/ISA/210) issued on Oct. 13, 2010, by Swedish Patent Office as the International Searching Authority for International Application No. PCT/SE2010/000177.

* cited by examiner

*Primary Examiner* — Monzer R Chorbaji
(74) *Attorney, Agent, or Firm* — Buchanan Ingersoll & Rooney PC (57) ABSTRACT

A device for sterilization of packages and a method of sterilizing packages are provided. The device comprises a gassing zone for exposing the packages to a gaseous sterilization agent, inlet mechanisms for introducing the gaseous sterilization agent into the gassing zone and a conveyor for transporting the packages through the gassing zone in a transport direction. The device also includes a separation mechanism arranged inside the gassing zone to divide at least an upper part of the gassing zone into sub gassing zones, each of said separation mechanisms having an opening for passage of the packages, each of at least a number of the inlet mechanisms being arranged to provide a flow of the gaseous sterilization agent at the opening of a respective one of the separation mechanisms.

17 Claims, 4 Drawing Sheets

DEVICE AND A METHOD FOR STERILIZATION OF PACKAGES

TECHNICAL FIELD

The present invention relates to a device for sterilization of packages. The device comprises a gassing zone for exposing the packages to a gaseous sterilization agent, inlet means for introducing the gaseous sterilization agent into the gassing zone and a conveyor for transporting the packages through the gassing zone in a transport direction. Further, the invention relates to a method of sterilizing packages.

TECHNICAL BACKGROUND

Within the food industry, beverages and other products are often packed in paper or paperboard based packages. Packages intended for liquid food are often produced from a packaging laminate comprising a core layer of paper or paperboard and an outer, liquid-tight layer of thermoplastic material on at least that side of the core layer which will form the inside of the packages.

One kind of frequently occurring packages are the so-called carton bottles. In substance, these are composed of a lower part in the form of a sleeve of packaging laminate like the one described above, and an upper part in the form of a plastic top having a neck which is provided with an opening/closing means, such as a screw cap.

The carton bottles are often produced in that sheets, so-called blanks, of packaging laminate are formed into tubes which are closed by sealing of two opposing edges of each sheet in an overlapping condition. Then, according to a first variant, a top of thermoplastic material is directly injection-moulded onto the tube at one end. The injection-moulded top could have a neck sealed by a membrane for subsequent provision of a screw cap. Alternatively, the top could be injection moulded using the screw cap as a part of the moulding cast. In such a case, the package is provided with the screw cap in connection with the injection moulding of the top. After injection-moulding, the package is filled, sealed at the open end of the tube for achieving a sleeve and closing the package, and formed into the desired shape.

According to a second variant, instead of injection-moulding a top directly onto the tube, the tube is slipped over a respective premade plastic top and arranged in such a way that a major part of the top protrudes from the tube. The premade top has a neck closed by a screw cap. After sealing of the top and the tube along a contact surface between them, the package is filled, sealed at the open end of the tube for achieving a sleeve and closing the package, and finally formed into the desired shape.

The above manufacturing methods are well-known in the art and will not be described in greater detail.

In order to extend the shelf-life of the packed product, it is known in the art to sterilize the packages before the filling operation. Depending upon the desired length of shelf-life, and depending upon whether the packages are to be distributed and stored in a refrigerated environment or at room temperature, different levels of sterilization may be selected.

As an example, chemical sterilization can be used for sterilizing open carton bottles before filling. One sterilization apparatus for gas phase sterilization of carton bottles is described in published international application WO2004/054883, which is hereby incorporated herein by reference. The patent specification discloses how the carton bottles are sterilized in that, disposed upside down on a conveyor belt, they are caused to pass first through a heating zone, then a sterilization zone and finally a venting zone. In the sterilization zone, the carton bottles are subjected to gaseous hydrogen peroxide. In order to prevent the hydrogen peroxide from condensing on the surface of the carton bottles in the sterilization zone, which impedes later removal, the carton bottles are heated up in the heating zone to a temperature above the dew point of the hydrogen peroxide gas. In the venting zone, the carton bottles are subjected to sterile hot air in order to vent off hydrogen peroxide which remains in and on the carton bottles. After sterilization, the interior of the carton bottles needs to be kept under aseptic conditions until filling with product and subsequently sealing.

To be able to achieve a satisfactory sterilization of the carton bottles, the conditions of the respective zones must be maintained. To this end, as described more closely in WO2004/054883, the zones are separated from each other by partitionings. Further, a higher pressure is maintained in the sterilization zone than in the heating and venting zones to prevent flows from the heating and venting zones into the sterilization zone.

In order to obtain a satisfactory sterilization of the carton bottles, they must be subjected to a sufficiently high sterilizing gas concentration for a sufficiently long time, i.e. a stable, sufficiently high hydrogen peroxide concentration should be maintained throughout the sterilization zone. Further, to maintain the positive pressure inside the sterilization zone, a very strong inflow into the sterilization zone is required because of the significant outflow through the partitionings separating the sterilization zone from the heating and venting zones, respectively. This will result in large emissions of gaseous hydrogen peroxide form the sterilization zone, which emissions require appropriate handling. Naturally, this will also result in a large consumption of hydrogen peroxide.

SUMMARY

An object of the present invention is to provide a device for sterilization of packages and a method of sterilizing packages which, at least partly, eliminate potential limitations of prior art. The basic concept of the invention is to ensure a stable, high concentration of gaseous sterilization agent essentially throughout a part of a gassing zone of the device and, at the same time, guarantee very small emissions of sterilization agent from the gassing zone as well as a relatively low consumption of sterilization agent. This is achieved by dividing the gassing zone into sub zones separated by blockages counteracting a flow between the sub zones, each of the blockages being composed of a physical separation means together with a flow of gaseous sterilization agent.

The device and the corresponding method for achieving the object above are defined in the appended claims and discussed below.

A device for sterilization of packages according to the present invention comprises a gassing zone for exposing the packages to a gaseous sterilization agent, inlet means for introducing the gaseous sterilization agent into the gassing zone and a conveyor for transporting the packages through the gassing zone in a transport direction. The device is characterized in further comprising separation means arranged inside the gassing zone to divide at least an upper part of the gassing zone into sub gassing zones. Each of said separation means has an opening for passage of the packages and each of at least a number of the inlet means is arranged to provide a flow of the gaseous sterilization agent at the opening of a respective one of the separation means.

Of course, the device can be used for sterilization of different types of packages, such as carton bottles of the above described type.

In the gassing zone, the packages should be exposed to a sufficiently high concentration of sterilization agent for a sufficiently long time to achieve a satisfactory sterilization of the inside and at least a part of the outside of the packages. This is because those parts of the surface of the packages are exposed in an aseptic zone directly following the gassing zone where, as the name implies, aseptic conditions should be maintained. In other words, everything that enters the aseptic zone must be commercially sterile.

Because of the provision of the separation means within the gassing zone, at least the upper part of the gassing zone is divided into sub gassing zones arranged in succession along the transport direction. Thus, the upper part of the gassing zone is a section extending in the longitudinal direction of the gassing zone. The sub gassing zones are separated from each other by blockages or "walls", each "wall" being formed of a separation means together with a flow of gaseous sterilization agent provided at the opening of the separation means. Thus, the flow of sterilization agent "closes" the opening of the separation means and the "wall" thereby formed counteracts a flow through the gassing zone in the transport direction and a direction opposite thereto. This arrangement renders it possible to attain and maintain a high concentration of gaseous sterilization agent in all the sub gassing zones, i.e. essentially throughout at least the upper part of the gassing zone, which, in turn, enables a stable and safe sterilization of the packages.

The inventive device can be so constructed that the flow of gaseous sterilization agent is essentially centered, in the transport direction, in the opening of said respective one of the separation means. Such a configuration maximizes the above mentioned counteraction to a flow between the sub gassing zones.

According to one embodiment of the invention, the device also has outlet means for evacuating the gaseous sterilization agent from the gassing zone. Further, in accordance herewith, the inlet means are arranged at an upper portion of the gassing zone while the outlet means are arranged at a lower portion of the gassing zone. Thereby, the flow at the opening of the separation means can be directed, in an unobstructed condition, from the upper to the lower portion of the gassing zone. By unobstructed condition is meant a condition where no object is "standing in the way" of the flow. This embodiment results in an improved flow control which in turn reduces the risk of recontamination of the packages.

The separation means of the inventive device may be formed in a number of different ways. In accordance with one embodiment of the invention, the separation means each comprise a set of baffles arranged in a common baffle plane. This common baffle plane is arranged essentially orthogonal to the transport direction through the gassing zone. This embodiment enables a mechanically simple and hygienic construction of the device. It should be stressed that the set of baffles can comprise any number of baffles, from a single one and up.

The inventive device can be such that a centre axis of each of the inlet means arranged to provide a flow of the gaseous sterilization agent at the opening of a respective separation means essentially coincides with the baffle plane of that separation means. Further, the inventive device can be such that each of these inlet means is arranged in the opening of the respective separation means. Such an inlet means arrangement enables a particularly effective and mechanically simple construction of the inventive device.

The device according to the present invention may, with advantage, be used in connection with RTF (Ready To Fill) packages, such as carton bottles as mentioned above. In accordance therewith, the device may be adapted for sterilization of the packages before filling of the packages through a respective open end of the same.

In accordance with one embodiment, the inventive device is adapted for intermittent operation, i.e. stepwise feeding of the packages to various stations for execution of different operations, such as sterilization and filling of the packages. In accordance therewith, the conveyor is arranged to transport the packages, with their respective open end facing the inlet means arranged to provide a flow of the gaseous sterilization agent at the opening of a respective separation means, in such a way that each of the packages is essentially centered, in the transport direction, in the opening of the respective separation means in a gassing step where gaseous sterilization agent is injected into the packages. This embodiment is advantageous since it facilitates reaching, for the purpose of sterilization, every nook inside the package with the gaseous sterilization agent. Further, it aids in obstructing a cross flow between the sub zones, which, in turn, facilitates the building-up of a high and stable concentration of gaseous sterilization agent within the different sub zones.

The device according to the invention can be such that each of the inlet means arranged to provide a flow of the gaseous sterilization agent at the opening of a respective separation means comprises a nozzle for injecting the gaseous sterilization agent into the packages through their respective open end, a delimited space for temporarily receiving the gaseous sterilization agent returning from the packages and a directing assembly for directing the returning gaseous sterilization agent out from the delimited space and along a respective outer surface of the packages in a direction from the respective open end of the packages. This arrangement is advantageous since it enables better flow control inside the gassing zone which in turn reduces the risk of recontamination of the the packages and improved possibilities of reusing the gaseous sterilization agent.

The device according to the invention can be constructed such that the gassing zone, in a direction orthogonal to the transport direction, has a cross section presenting a restriction or constriction between the upper part and a lower part. As an example, the cross section can be hour glass shaped. This gassing zone configuration is advantageous since it promotes a one-way flow, from the upper to the lower portion of the gassing zone at the restriction, which in turn may prevent recontamination of the packages.

In accordance with one embodiment the separation means may be arranged to extend in both the upper part and the lower part of the gassing zone to divide the upper and lower parts of the gassing zone into sub gassing zones. Such an embodiment means that a sub gassing zone comprises a respective portion of the upper and lower parts and the restriction of the gassing zone. This embodiment is advantageous since it renders it possible to attain and maintain a high concentration of sterilization agent throughout both the upper and the lower part of the gassing zone which, in turn, further reduces the risk of recontamination of the packages.

According to one embodiment of the present invention, the device is constructed such that a slit is provided between each of said separation means and interior walls of the device at the gassing zone. This feature is favorable since it facilitates cleaning of the device.

A method of sterilizing packages according to the present invention comprises introducing a gaseous sterilization agent into a gassing zone of a device for sterilization of packages, transporting the packages through the gassing zone in a transport direction, and exposing, in the gassing zone, the packages to the gaseous sterilization agent. The method is characterized in further comprising transporting the packages through a respective opening of a plurality of separation means arranged inside the gassing zone to divide at least an upper part of the gassing zone into sub gassing zones, and providing a flow of the gaseous sterilization agent at the opening of at least a number of the separation means.

The characteristics discussed in connection with the inventive device are, of course, transferable to the inventive method. Further, these characteristics may naturally be combined in the same embodiment.

DETAILED DESCRIPTION

In the following, the term (adequate or the like) sterile is taken to signify that the package, after sterilization, attains a level of sterilization which is designated commercially sterile.

Figure 1:
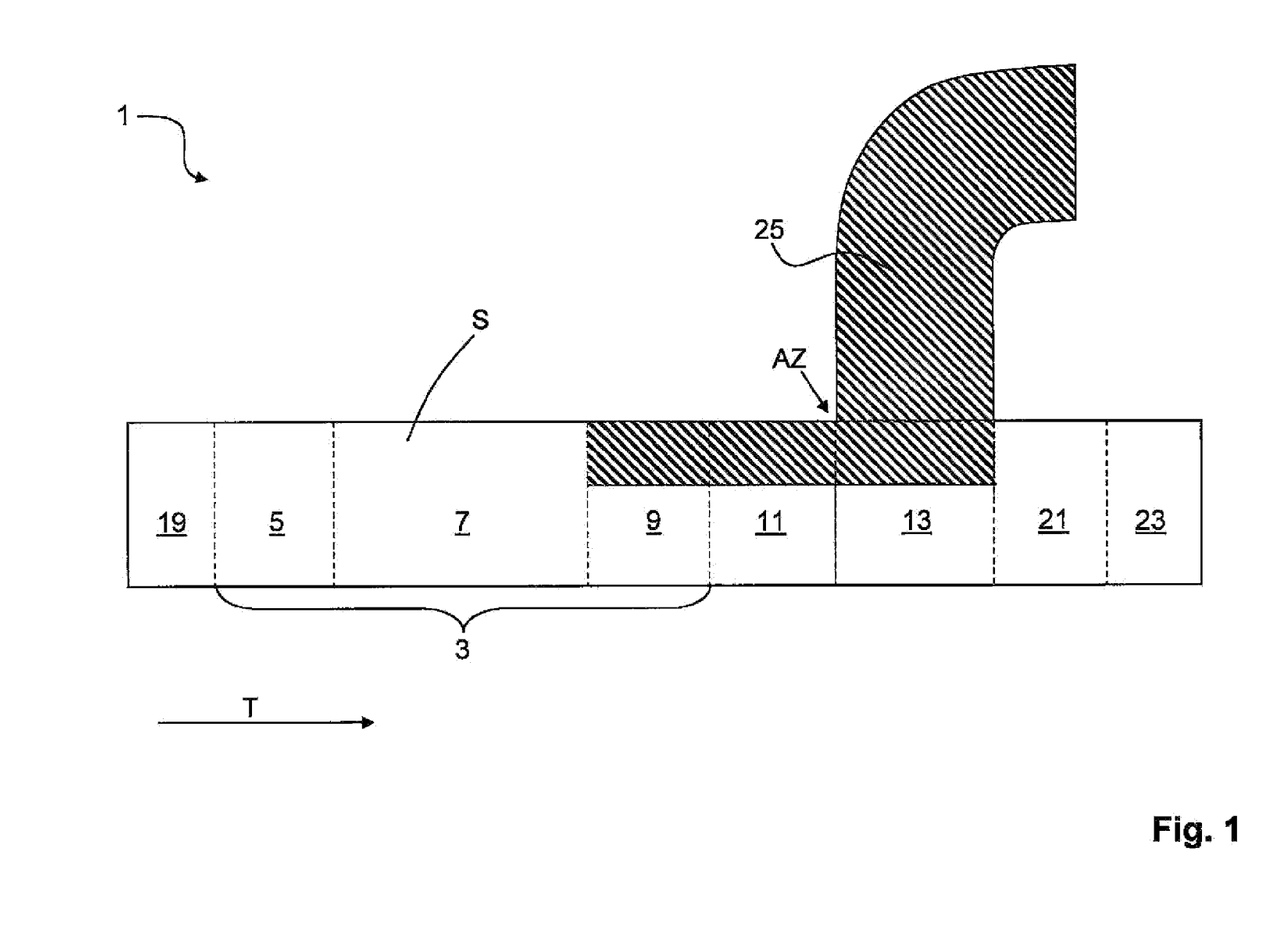
FIG. 1 is a schematic side view of a device according to a one embodiment of the present invention.
Figure 2:
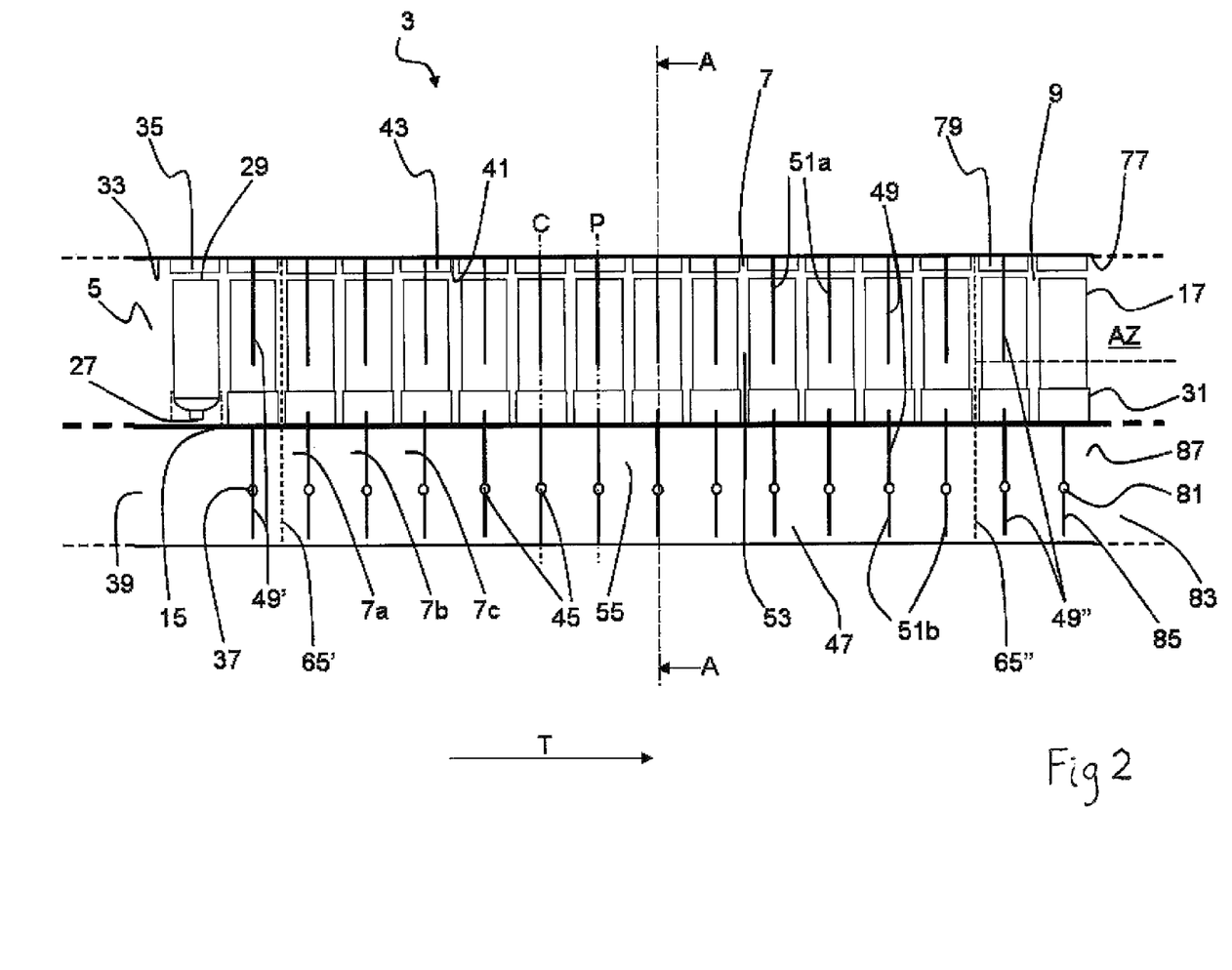
FIG. 2 is a schematic side view of a part of the device shown in FIG. 1, with a side wall removed for illustrative purposes.

In FIG. 1, a device 1 for sterilization of packages according to one embodiment of the present invention is shown. The device 1 is adapted for gas phase sterilization of packages in the form of carton bottles of the initially described type. The device 1 comprises a tunnel 3, in turn, comprising a preheating zone 5, a gassing zone 7 and a venting zone 9. A part of this tunnel 3 is illustrated in more detail in FIG. 2 with a side wall S removed for illustrative purposes. The device 1 also includes a filling zone 11, a sealing zone 13 and a conveyor 15 for transporting the carton bottles 17 (shown only in FIG. 2) through the various zones in a transport direction T. Further, the device 1 has an infeed station 19, a final folding station 21 and an outfeed station 23 for the carton bottles 17, which stations will not be described in detail herein. The same goes for an arrangement 25 for supplying sterile air to the device 1, which arrangement is described in detail in Swedish copending patent application filed by the applicant on the same date as the present application and titled "Device for cleaned air provision" (SE-0900908-5), which application is hereby incorporated herein by reference. The boundaries between the zones, and the zones and the stations, have been illustrated with broken lines in the figures. As apparent from FIG. 2, the carton bottles 17 are arranged upside-down, with their respective closed end 27 facing the conveyor 15 and the open end 29 directed upwards, in carrier means 31 attached to the conveyor 15. For illustrative purposes, the first carrier means in FIG. 2 is has been drawn transparent.

The gassing and venting zones, 7 and 9, respectively, of the tunnel 3 has an hour glass shaped cross section, i.e. a narrow center part, in a direction orthogonal to the transport direction T. This is apparent form FIGS. 3a-b which illustrate a cross section through the gassing zone 7 along the line A-A in FIG. 2. The purpose of the hour glass shaped cross sections will be further discussed below and is disclosed in detail in Swedish copending patent application filed by the applicant on the same date as the present application and titled "A device and a method for maintaining a gas flow barrier between two volumes of a channel" (SE-0900913-5), which application is hereby incorporated herein by reference.

From a ceiling 33 of the preheating zone 5, a number of inlet means 35 for introduction of hot filtered air extend. Further, a number of outlet means 37 for evacuation of the hot filtered air are arranged in a lower portion 39 of the preheating zone 5. This arrangement promotes a flow inside the preheating zone in a direction orthogonal to the transport direction.

From an upper portion, more particularly a ceiling 41, of the gassing zone 7, a number of inlet means 43 for introduction of a gaseous sterilization agent, here hydrogen peroxide, extend. The inlet means 43 are arranged in line in the transport direction T at the center of the ceiling 41 with a fixed mutual distance. A number of outlet means 45 for evacuation, by suction, of the gaseous hydrogen peroxide are arranged in a lower portion 47 of the gassing zone 7. Each of the outlet means 45 is arranged in line with a respective one of the inlet means 43. Thus, the number of inlet means 43 inside the gassing zone 7 is equal to the number of outlet means 45 inside the gassing zone 7. The above arrangement promotes a flow inside the gassing zone in a direction orthogonal to the transport direction.

Figure 3A:
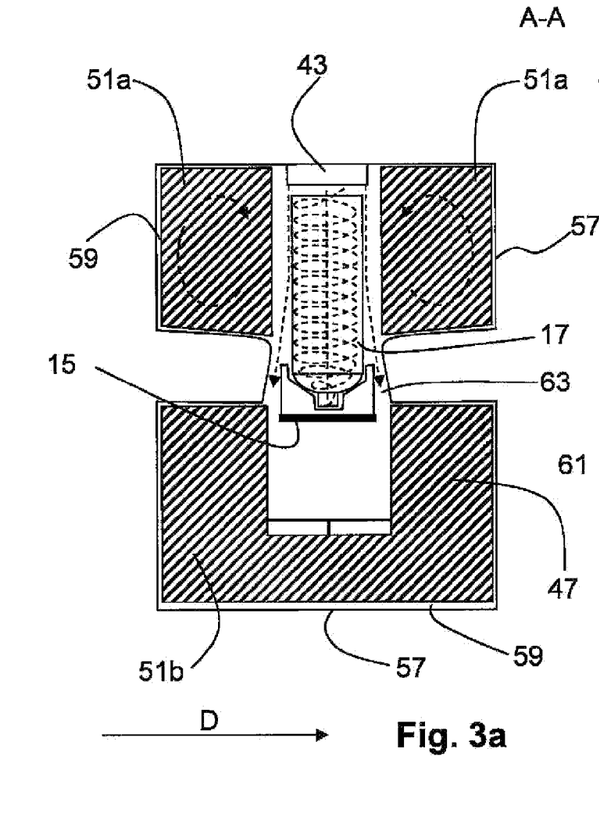
FIG. 3a-b schematically illustrates cross sections of the device taken along the line A-A shown in FIG. 2
Figure 3B:
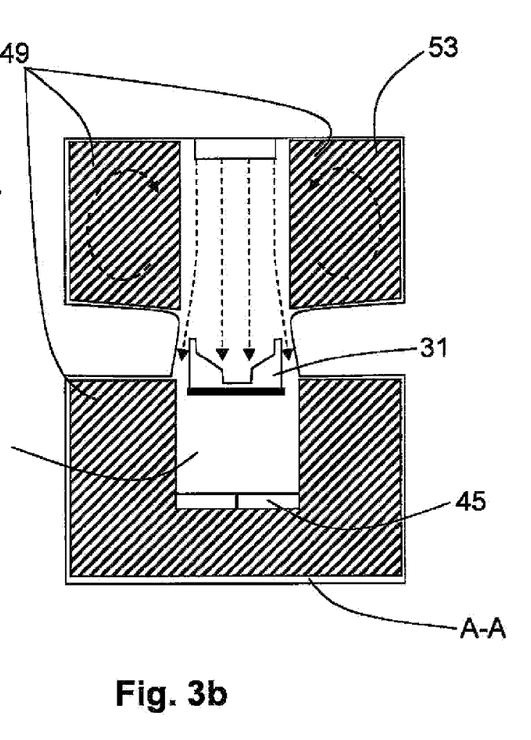

Further, as illustrated in FIGS. 2 and 3a-b, a number of separation means 49 in the form of sets of baffles 51 (51a+51b) are arranged inside the gassing zone 7, with a fixed mutual distance, to divide it into sub gassing zones 7a, 7b, 7c and so on. Thus, a sub gassing zone corresponds to the space between two separation means 49 (with the exception of the two end sub zones as will be further explained below). The baffles of a baffle set are arranged in a common baffle plane P which is essentially orthogonal to the transport direction T. The baffle sets each contains three baffles; two upper baffles 51a adapted for arrangement in an upper part 53 of the gassing zone 7, and one lower baffle 51b adapted for arrangement in a lower part 55 of the gassing zone 7. As apparent from the figures, the baffles do not extend all the way to the walls 57 of the device 1 except for in some contact points (not shown). The thus created slits 59 are provided for facilitating washing of the device. The slit towards the lower wall is generally slightly larger in order to allow for adequate drainage of detergent.

Each of the separation means 49 has an opening 61 for passage of the conveyor 15, the carton bottles 17 and the carrier means 31. This opening 61 is formed by the baffles of a baffle set having a particular design and being arranged in a certain way in relation to each other. Each of the inlet means 43 is associated with one of the separation means 49 and arranged in the opening 61 thereof, centered in the transport direction T. More particularly, a centre axis C of the inlet means 43 essentially coincides with the baffle plane of the respective separation means 49. Therefore, each of the inlet means 43 is arranged to provide, in an unobstructed condition, a flow of gaseous hydrogen peroxide that essentially fills at least the entire upper part of the opening 61 of the corresponding separation means. FIG. 3b illustrates the case of an empty carrier means 31 present in the opening 61. Here the hydrogen peroxide flow fills essentially the entire opening 61, at least in the upper part 53 of the gassing zone 7. In other words, the gas flow together with the baffles 51 of the separation means form a partitioning inside the gassing zone 7 arranged to counteract a flow through the gassing zone 7 in the transport direction T and a direction opposite thereto. FIG. 3a shows the case of a carton bottle 17 arranged in a carrier means 31 present in the opening 61. As apparent from this figure, the flow of gaseous hydrogen peroxide from the inlet means 43, together with the carton bottle 17, here fills essentially the entire opening 61 of the separation means 49, at least in the upper part 53 of the gassing zone 7. In other words, a partitioning like the one described above is here formed by the gas flow, the baffles and the carton bottle. Thus, irrespective of whether or not a carton bottle is arranged below the inlet means, a corresponding partitioning will always exist because of the continuous flow of gaseous hydrogen peroxide provided by the inlet means and the presence of the corresponding separation means.

The partitionings inside the gassing zone 7 will act as gas locks between the sub gassing zones 7a, 7b, 7c . . . . Because of these gas locks, the concentration of hydrogen peroxide inside all the different sub zones can be brought to, and maintained at, a stable, high level. At least in the upper part, the level will be high enough for adequate sterilization of at least the inside and parts of the outside of the carton bottles when present, for a certain period of time, in the gassing zone. The hydrogen peroxide concentration within the different sub zones will be about the same essentially throughout the gassing zone even if it will decrease slightly at the two end sub zones because of some gas exchange with the preheating and venting zones, respectively, which will be further discussed below. Moreover, the hydrogen peroxide concentration in the sub gassing zones will be somewhat higher in the upper part than in the lower part thereof.

The gas locks between the sub gassing zones exist irrespective of whether a carton bottle and a carrier means or just a carrier means is present in the respective opening or not. Of course, the presence of a carton bottle will affect the flow in the opening, the two major effects being that some components of the flow from the inlet means 43 will be directed into the carton bottle 17 and will thus not reach the narrow center part unaffected, and that the carton bottle will occupy part of the narrow center part and thus influence the flow velocity there through. However, the general experience from simulations as well as experiments made is that establishment of the gas locks is not a problem when carton bottles are occupying the carrier means. Rather, the carton bottles assist in blocking unwanted flows in transport direction and the direction opposite thereto, and aid in guiding the flow from the inlet means in a direction orthogonal to the transport direction.

As previously mentioned, a part of the tunnel 3 has an hour glass shaped cross section in a direction orthogonal to the transport direction T, the purpose of which now will be discussed with reference to the gassing zone 7 and FIGS. 3a-b. As apparent from the figures, the upper part 53 and the lower part 55 are connected by a narrow center part, a so-called restriction 63. This restriction 63 is positioned between the upper baffles 51a and the lower baffle 51b and "closes" the space between the same in a direction orthogonal to the transport direction T. Thereby, the restriction 63 inherently promotes the generation of the gas locks between the sub gassing zones. Further, the restriction 63 is arranged to create a pressure difference between the upper part 53 and the lower part 55 of the gassing zone 7, more particularly, a higher pressure within the upper part than within the lower part. This is to provide for better definition of the flows inside the sub zones and, especially, facilitate the creation of a gaseous hydrogen peroxide flow directed essentially from the ceiling 41 and downwards in the restriction of the sub zones. As mentioned above, also the venting zone has an hour glass shaped cross section. Naturally, also the restriction of the venting zone is arranged to create a pressure difference between the upper and lower parts of the venting zone to create a flow directed essentially from the ceiling 77 and downwards in the restriction of the venting zone.

The number of separation means 49 inside the gassing zone 7 is equal to the number of inlet means 43 inside the gassing zone 7. Further, as shown in FIG. 2, an additional separation means 49', 49" of the above described type is arranged in the preheating zone 5, and the venting zone 9, respectively, adjacent to the gassing zone 7. The borderline between the preheating zone 5 and the gassing zone 7 runs between the separation means 49' and the first separation means 49 inside the gassing zone 7, as illustrated by the dashed line 65'. Similarly, the borderline between the gassing zone 7 and the venting zone 9 runs between the last separation means 49 inside the gassing zone and the separation means 49", as illustrated by the dashed line 65". Thereby, the two end sub zones of the gassing zone corresponds to half the space between the first separation means inside the gassing zone 7 and the separation means 49' inside the preheating zone 5 and between the last separation means inside the gassing zone and the separation means 49" inside the venting zone 9, respectively. Since, as is clear from FIG. 2, the end sub zones are "open" towards the preheating and venting zones, some gas exchange between these zones is enabled resulting in a slightly lower hydrogen peroxide concentration within the end sub gassing zones, as was mentioned above.

Figure 4:
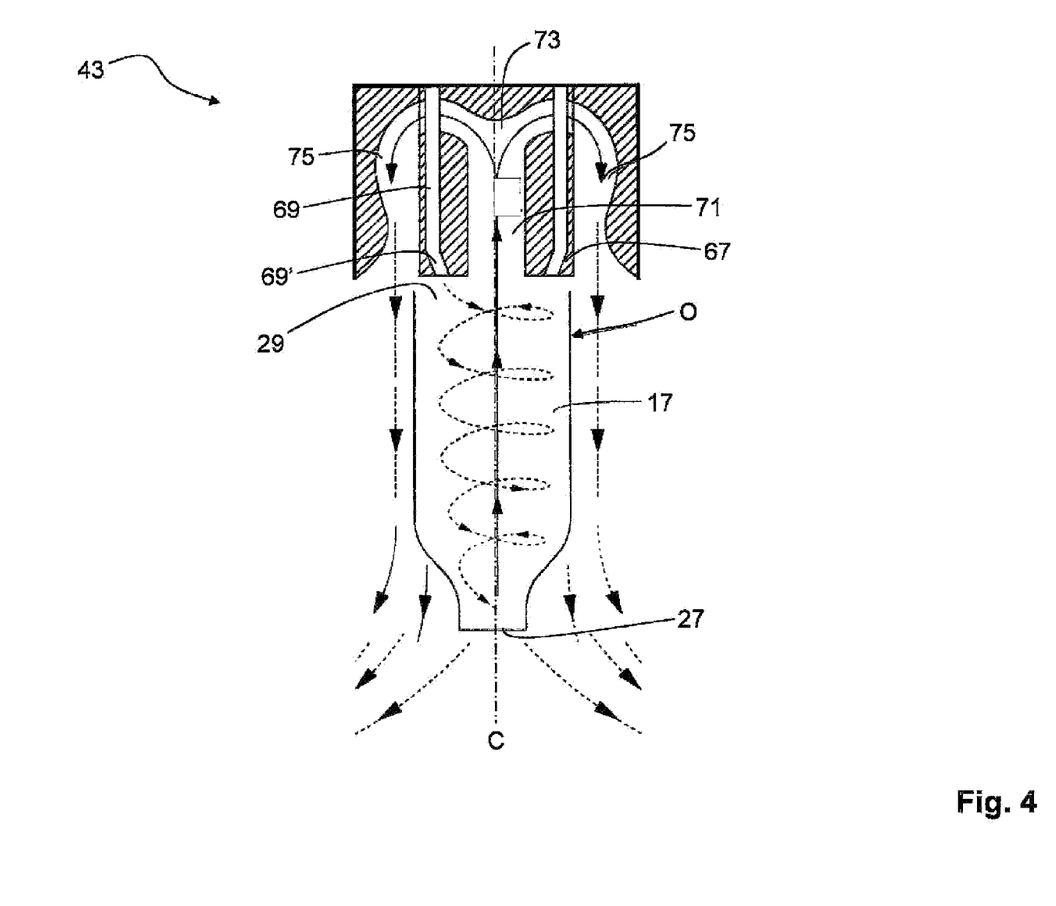
FIG. 4 is a cross sectional view of an inlet means that with advantage can be used in connection with the present invention.

In FIG. 4, one of the inlet means 43 of the gassing zone 7 is schematically illustrated. The inlet means 43 comprises a nozzle 67 for injecting the gaseous hydrogen peroxide into the carton bottles 17 (schematically illustrated), through the respective open end 29 thereof, in a gassing step during which the carton bottles 17, as illustrated in FIGS. 2 and 3a, are essentially centered, in the transport direction T, and a direction D orthogonal thereto, in the openings 61 of the corresponding separation means 49, i.e. arranged just below, and in line with, the inlet means 43. To this end, the nozzle 67 comprises a number of supply channels 69 which are distributed around the center axis C of the inlet means 43. The last part 69' of the supply channels 69 is, as apparent from FIG. 4, inclined towards the centre axis C. This inclination gives rise to a helical flow of gaseous hydrogen peroxide inside the carton bottles 17, along the periphery thereof. When the flow reaches the closed end 27 of the carton bottles 17, it will, as a consequence of the lower gas pressure in the centre of the carton bottle, strive to leave the carton bottle through the center of the same.

The inlet means 43 further comprises a delimited space 71, in the form of a return channel through the nozzle 67, for receiving the gas flow leaving the carton bottle 17. The inlet means 43 further includes a directing assembly 73, comprising a number of directing channels 75 distributed around the center axis C of the inlet means, for directing the gas flow leaving the carton bottle 17 out from the delimited space 71 and along a respective outer surface O of the carton bottle in a direction from the respective open end 29 of the same. Thus, the gas flow returning from the carton bottle 17 enters first the return channel and then the directing assembly 73 where it is deflected approximately 180° before being led out along the exterior of the carton bottle 17. The flow created inside and outside the carton bottle is schematically illustrated by the dashed lines and the arrows.

The helical flow that is formed by the inlet means 43 makes it possible to reach every nook and corner inside the carton bottles 17 with the hydrogen peroxide gas since the flow works its way through the carton bottle, all the way down to the closed end 27 of the same. In turn, this enables an adequate sterilization of the carton bottle inside. This would not be easy to achieve using an inlet means creating a straight, downwards directed flow of hydrogen peroxide gas, especially not in connection with the geometry of carton bottles of the present kind. Further, because of the redirection of the returning flow, an essentially downwards directed flow outside the carton bottles is promoted which reduces the risk of recontamination of the carton bottle surfaces that is to be sterilized. Additionally, the inlet means 43 obviously offers an opportunity to reuse the hydrogen peroxide gas. The inlet means 43 is described in detail in applicant's copending application WO2007/024173, which is hereby incorporated herein by reference.

Further, as shown in FIG. 2, from a ceiling 77 of the venting zone 9, a number of inlet means 79 for introduction of hot sterile air extend. Further, a number of outlet means 81 for air evacuation are arranged in a lower portion 83 of the venting zone 9. This arrangement promotes a flow inside the venting zone in a direction orthogonal to the transport direction. Also, a number of baffles 85 are arranged inside the venting zone 9 with a fixed mutual distance. The baffles 85 are arranged essentially orthogonal to the transport direction T and in a lower part 87 of the venting zone 9. The baffles 85 are similar to the lower baffles 51b arranged in the lower part 55 of the gassing zone 7. The purpose of the baffles 85 in the venting zone 9 is to conteract a flow through the venting zone in the transport direction an a direction opposite thereto while further promoting a flow in a direction orthogonal to the transport direction to render the venting more efficient and minimize the risk of recontamination of the carton bottles. Thus, an important function of the baffles 85 is to assist in maintaining the desired aseptics, which will be further described below.

The inlet means 35, 43 and 79 in the preheating zone 5, gassing zone 7 and venting zone 9, respectively, do not have to be, but are in the presently described embodiment, all of the same kind, i.e. of the kind described with reference to FIG. 4. Use of such inlet means also in the preheating and venting zones enables particularly effective preheating and venting of the carton bottles. Similarly, the outlet means 37, 45 and 81 in the different zones, do not have to be, but are in the presently described embodiment, all of the same kind, which kind is not described in detail herein.

An upper part of the venting zone 9 forms, together with upper parts of the filling and sealing zones 11 and 13, respectively, and at least a part of the arrangement 25 an aseptic zone AZ, see FIGS. 1 (scored area) and 2 inside which, as indicated by the name, aseptic conditions should be maintained. Thus, the inside and a part of the outside of the carton bottles, which are exposed inside the aseptic zone, should be kept under aseptic conditions until the carton bottles have been filled and sealed. In the case of the venting zone part of the aseptic zone, such aseptic conditions can be maintained thanks to the flow directed essentially from the ceiling 77 and downwards in the restriction, in turn, created by means of the inlet means 79, outlet means 81, the hour glass shaped cross section of the venting zone and the lower baffles 85.

Next, to further illustrate the device 1 according to the invention as well as a corresponding method according to the invention, the journey of the carton bottles through the tunnel 3 of the device 1 will now be described.

The device 1 operates intermittently, i.e. the carton bottles are fed, not with a continuous movement, but in a step-wise manner by double indexing, through the different zones arranged in respective carrier means 31, in turn arranged on a conveyor 15. Of course, for various reasons, a carrier means 31 can be empty and not carry a carton bottle. However, in the following it is assumed that all carrier means are carrying a respective carton bottle.

First, the carton bottles 17 enter the preheating zone 5 comprising a number of preheating stations corresponding to the inlet means 35 arranged to provide a respective continuous flow of hot filtered air. The carton bottles are fed in the transport direction T until they are positioned just underneath a respective one of the inlet means 35. Then, the feeding is stopped for a predetermined time for performing a preheating step during which the inlet means 35 inject hot filtered air directly into the carton bottles 17. Thereafter, the feeding of the carton bottles in the transport direction T is resumed and maintained until the carton bottles are positioned just underneath the second next inlet means 35. Then, the feeding is stopped again for performing another preheating step. This procedure is repeated until the carton bottles leave the preheating zone 5. Thus, because of the double indexing, the carton bottles will be subjected to a preheating step by every two inlet means 35. Passing through the preheating zone 5, the carton bottles 17 are gradually heated to a temperature above the dew point of the sterilization agent, here hydrogen peroxide, to be used for the sterilization of the carton bottles. Condensing of hydrogen peroxide on the surfaces of the carton bottles in connection with subsequent hydrogen peroxide exposure can thereby be prevented.

After preheating the carton bottles 17 enter the gassing zone 7 comprising a number of gassing stations corresponding to the inlet means 43. The carton bottles 17 are fed in the transport direction T until they are positioned just underneath a respective one of the inlet means 43, i.e. centered, in the transport direction T, in the opening 61 of the corresponding separation means 49. Then, the feeding is stopped for a predetermined time for performing a gassing step during which the inlet means 43 inject gaseous hydrogen peroxide directly into the carton bottles 17. In this position, a respective longitudinal axis of the carton bottles essentially coincides with the baffle plane P of the separation means 49 and the center axis C of the inlet means 43, and the carton bottle 17, the carrier means 31 and the baffles 51a+b cover as much of the gassing zone cross section as possible. Thereafter, the feeding of the carton bottles 17 in the transport direction T is resumed and maintained until the carton bottles are positioned just underneath the second next inlet means 43. Then, the feeding is stopped again for performing another gassing step. This procedure is repeated until the carton bottles 17 leave the gassing zone 7. Just like in the preheating zone 5, the carton bottles 17 will be subjected to a gassing step by every two inlet means 43. Passing through the gassing zone 7, the inside and at least a part of the outside of the carton bottles are gradually sterilized to a level of sterilization which is designated commercially sterile. To attain this level of sterilization, the carton bottles must be subjected to gas of a sufficiently high hydrogen peroxide concentration for a sufficiently long time. The device, and more particularly the gassing zone of the same, has been constructed in such a way that this objective can be achieved.

As described above, the purpose of the separation means 49 inside the gassing zone is to counteract, together with the gas flow from the inlet means 43, a flow through the gassing zone in the transport direction T and a direction opposite thereto, while promoting a flow in a direction orthogonal to the transport direction. Notwithstanding this, there is still a very limited possibility for particles to move through the gassing zone in the transport direction T, from the preheating zone 5 to the venting zone 9. However, the construction and operation of the device 1 is inherently such that it is impossible for any particle to move faster through the gassing zone 7 than the carton bottles 17. Simulations and experiments have confirmed this. Therefore, since the hydrogen peroxide exposure time and concentration is enough for satisfactory sterilization of the carton bottles, the particles succeeding in moving through the gassing zone will also be sterilized to a sufficient degree. Thus, they will not jeopardize the sterile conditions in the aseptic zone AZ following the gassing zone 7.

Further, as described above, when a carton bottle 17 is positioned underneath one of the inlet means 43, gaseous hydrogen peroxide is injected therein to sterilize the inside of the package. The hydrogen peroxide gas returning from the carton bottle 17 is collected and redirected by the inlet means 43 along at least a part of the outside of the carton bottle. Between two gassing steps, the carton bottle 17 is moved to the second next inlet means 43. During this movement, because of the strong jets from the inlet means 43, surrounding gas in the gassing zone 7 will be drawn into the carton bottle through the open end 29 thereof. Because of the inventive construction of the gassing zone 7, the hydrogen peroxide concentration essentially throughout the gassing zone, i.e. also between the inlet means 43, can be brought to, and maintained at, a high level. Consequently, between two gassing steps, the inside of the carton bottle will actually be further sterilized. Also, when the carton bottle is travelling through the gassing zone 7, not only its inside is sterilized but also at least a part of its outside because of the sufficiently high hydrogen peroxide concentration maintained throughout the gassing zone. In case the hydrogen peroxide concentration were not stable and sufficiently high throughout the gassing zone, a transportation of the carton bottle through an area of the gassing zone with a relatively low, insufficient hydrogen peroxide concentration would result in a lowering of the sterilization degree of not only the outside but also the inside of the carton bottle because of the gas exchange between the interior and exterior of the carton bottle.

After gassing the carton bottles 17 enter the venting zone 9 comprising a number of venting stations corresponding to the inlet means 79. The carton bottles are fed in the transport direction T until they are positioned just underneath a respective one of the inlet means 73. Then, the feeding is stopped for a predetermined time for performing a venting step during which the inlet means 79 inject hot sterile air directly into the carton bottles 17. In this position, a respective longitudinal axis of the carton bottles essentially coincides with the baffles 85 arranged in the lower part 87 of the venting zone 9. Thereafter, the feeding of the carton bottles in the transport direction T is resumed and maintained until the carton bottles 17 are positioned just underneath the second next inlet means 79. Then, the feeding is stopped again for performing another venting step. This procedure is repeated until the carton bottles 17 leave the venting zone 9. Just like in the previous zones, the carton bottles will be subjected to a venting step by every two inlet means 73. Passing through the venting zone 9, residues of hydrogen peroxide inside and on the inside and outside surface of the carton bottles are gradually removed, an operation that is facilitated by the preheating operation inside the preheating zone 5 for preventing hydrogen peroxide condensing on the carton bottle surfaces.

As previously described, when the carton bottles 17 enter the venting zone 9, a respective portion of them also enters the aseptic zone AZ, which reaches beyond the final sealing of the carton bottles. As shown in FIG. 2, the lower boundary of the aseptic zone AZ runs above the carrier means 31, at predetermined distance therefrom, i.e. at an intermediate part of carton bottle sleeves. By the sterilization operation, the inside surface of the carton bottles as well as that part of the outside surface of the carton bottles that protrudes from the carrier means is commercially sterilized. Therefore, by defining the lower boundary of the aseptic zone AZ in the above described way it can be guaranteed that the carton bottle surfaces exposed inside the aseptic zone are commercially sterile.

In prior art solutions regarding sterilization, focus has been to achieve a proper concentration of sterilization agent inside the packages. This is of course a requirement for the present invention too. However, the present invention also enables increase of the concentration of sterilization agent outside of the package in the gassing zone. This will enable a proper sterilization of at least a part of the outside of the packages. As mentioned above, this will also have the beneficial effect of eliminating the risk of insufficient sterilization of the package inside if surrounding gasses are introduced into the package in connection with transportation of the same through the gassing zone. Such introduction of surrounding gasses will instead contribute to the sterilization of the inside of the packages. As explained in detail above, this huge advantage is obtained by the arrangement of baffles inside the gassing zone, and especially, the arrangement of the baffles in a specific relation to the inlet means in the gassing zone. This arrangement prevents a draught through the gassing zone which otherwise may result from the carton bottle movement therethrough. Further, it promotes a flow through the gassing zone essentially in a direction orthogonal to the transport direction. In all, this enables achievement of a stable and high hydrogen peroxide concentration throughout the gassing zone which, in turn, enables adequate sterilization of the carton bottles and secures aseptic zone integrity.

Thus, despite of the open nature of the device according to the invention it is very robust in that a stable and sufficiently high concentration of hydrogen peroxide can be obtained in the gassing zone of the same, which enables a better and more reliable sterilization of the packages. Further, since the inventive system is constructed so that a a flow through the gassing zone in the transport direction and a direction opposite thereto is counteracted, the emissions of gaseous sterilization agent to the preheating and venting zones, and thereby the surroundings, can be brought to a minimum. In turn, this results in a relatively low consumption of sterilization agent.

The above described embodiment should only be seen as an example. A person skilled in the art realizes that this embodiment can be modified and varied in a number of ways without deviating from the inventive conception.

As an example, in the above described embodiment, the separation means 49 extends in both the upper part 53 and the lower part 55 of the gassing zone 7 and, consequently, the sub gassing zones 7a, 7b, 7c . . . thus formed also extends in the upper and lower parts of the gassing zone. Thereby, a high and stable concentration of hydrogen peroxide can be obtained and maintained throughout the gassing zone, i.e. in both the upper and lower parts thereof. According to an alternative embodiment, the separation means, and thereby the sub gassing zones, could instead be arranged so as to extend in the upper part of the gassing zone only. With such an arrangement, a high and stable hydrogen peroxide concentration can not be guaranteed in the lower part of the gassing zone. In such an embodiment, an aseptic barrier extending in the transport direction in the gassing zone could be secured to protect the aseptics of an upper portion of gassing zone. Such an aseptic barrier could be secured, e.g. by an increased flow from the inlet means in the gassing zone, at the lower end of the separation means, i.e. at the restriction between the upper and lower parts of the gassing zone, to prevent particles from moving from the lower to the upper part of the gassing zone. As an example, the aseptic barrier inside the gassing zone could be positioned so as to be a prolongation of the lower boundary of the aseptic zone AZ. As an alternative, the aseptic barrier inside the gassing zone could be positioned below (but for obvious reasons not above) the lower boundary of the aseptic zone. If no aseptic barrier is secured inside the gassing zone, there could be a risk of possibly unsterile particles entering the upper portion of the gassing zone from a lower portion of the same. From the upper portion of the gassing zone, these particles could then enter the aseptic zone AZ following the gassing zone 7. Obviously, that would jeopardize the aseptic conditions inside the aseptic zone.

Further, the device according to the above described embodiment is adapted for intermittent operation. However, it should be understood that the device could also be adapted for non-intermittent, i.e. continuous, operation.

Additionally, the inlet means in the preheating, gassing and venting zones of the device according to the above described embodiment are of the kind generating a helical flow and redirecting the flow returning from the package. Of course, this kind of inlet means is just one of many that can be used in connection with the present invention. Similarly, other sterilization agents than hydrogen peroxide can be used in connection with the present invention.

Above, the number of inlet means 43 is equal to the number of outlet means 45 inside the gassing zone 7. Further, the number of inlet means 43 is equal to the number of separation means 49 inside the gassing zone 7. Naturally, alternative configurations are possible here. As an example, additional inlet means could be arranged inside the sub gassing zones, between the separation means.

Further, above, each of the outlet means 45 is arranged in line with a respective one of the inlet means 43 and a center axis C of the inlet means 43 essentially coincides with the baffle plane of the respective separation means 49. Of course, this need not be the case. According to alternative embodiments, the inlet and/or the outlet means can be off-set in relation to each other and/or the baffle planes.

The above described baffle sets each contain three baffles; two upper baffles and a lower one. Of course, a baffle set can contain any number of baffles. As an example, a baffle set may contain one single baffle extending in both the upper and the lower part of the gassing zone, said single baffle being provided with an opening for passage of the conveyor, carton bottles and carrier means. As another example, a baffle set may contain four baffles, two similar upper ones and two similar lower ones.

In the above described embodiment, the gassing and venting zones have an hour glass shaped cross section in a direction orthogonal to the transport direction, i.e. there is a restriction or constriction between the upper and lower parts of the zones. Naturally, other such cross section shapes are possible. As an example, two opposing plates projecting from a respective side wall of the tunnel and separated by a predetermined distance could instead be used for forming the restriction. Moreover, cross sections without a restriction are also possible. As an example, the cross section could be rectangular and the baffle sets could cover as much as possible of the cross section.

Further, in the above described embodiment, the concentration of gaseous sterilization agent is higher in the upper part of the gassing zone than in the lower part thereof. This need not be the case. In an alternative embodiment the sterilization agent concentration is the same in the upper and lower parts of the gassing zone. For example, this can be achieved by reducing the slits between the lower baffles and the walls of the device and/or by increasing the inflow of hydrogen peroxide into the gassing zone.

Finally, the inventive device may be used for sterilization of other packages than carton bottles.

It should be stressed that a description of details not relevant to the invention has been omitted and that the figures are not drawn according to scale.

The invention claimed is:

1. A device for sterilization of packages comprising a gassing zone for exposing the packages to a gaseous sterilization agent, inlet means for introducing the gaseous sterilization agent into the gassing zone and a conveyor for transporting the packages through the gassing zone in a transport direction, separation means arranged inside the gassing zone to divide at least an upper part of the gassing zone into sub gassing zones, each of said separation means having an opening for passage of the packages, each of at least a number of the inlet means being aligned along the transport direction with a respective one of the separation means to provide a flow of the gaseous sterilization agent at the opening of the respective one of the separation means.

2. A device according to claim 1, wherein said flow of the gaseous sterilization agent is essentially centered, in the transport direction, in the opening of said respective one of the separation means.

3. A device according to claim 1, further comprising outlet means for evacuating the gaseous sterilization agent from the gassing zone, said at least a number of the inlet means being arranged at an upper portion of the gassing zone and said outlet means being arranged at a lower portion of the gassing zone.

4. A device according to claim 1, wherein the separation means each comprise a set of baffles arranged in a common baffle plane which is essentially orthogonal to the transport direction through the gassing zone.

5. A device according to claim 4, wherein a centre axis of each of said at least a number of the inlet means essentially coincides with the baffle plane of said respective one of the separation means.

6. A device according to claim 1, wherein each of said at least a number of the inlet means is arranged in the opening of said respective one of the separation means.

7. A device according to claim 1, adapted for sterilization of the packages before filling of the packages through a respective open end of the same.

8. A device according to claim 7, adapted for intermittent operation, wherein the conveyor is arranged to transport the packages, with their respective open end facing said at least a number of the inlet means, in such a way that each of the packages is essentially centered, in the transport direction, in the opening of said respective one of the separation means in a gassing step where gaseous sterilization agent is injected into the packages.

9. A device according to claim 7, wherein each of said at least a number of the inlet means comprises a nozzle for injecting the gaseous sterilization agent into the packages through their respective open end, a delimited space for temporarily receiving the gaseous sterilization agent returning from the packages and a directing assembly for directing the returning gaseous sterilization agent out from the delimited space and along a respective outer surface of the packages in a direction from the respective open end of the packages.

10. A device according to claim 1, wherein the gassing zone, in a direction orthogonal to the transport direction; has a cross section presenting a restriction between the upper part and a lower part.

11. A device according to claim 10, wherein the separation means extends in both the upper part and the lower part of the gassing zone to divide the upper and lower parts of the gassing zone into sub gassing zones.

12. A device according to claim 1, wherein a slit is provided between each of said separation means and interior walls of the device at the gassing zone.

13. A method of sterilizing packages comprising introducing a gaseous sterilization agent by way of a plurality of inlets into a gassing zone of a device for sterilization of packages, transporting the packages through the gassing zone in a transport direction, and exposing, in the gassing zone, the packages to the gaseous sterilization agent, transporting the packages through a respective opening of a plurality of separation means arranged inside the gassing zone to divide at least an upper part of the gassing zone into sub gassing zones, each of the inlets being aligned along the transport direction with a respective one of the separation means, and providing a flow of the gaseous sterilization agent at each of the openings of at least a number of the separation means by way of a respective one of the inlets.

14. A method according to claim 13, further comprising providing said flow of the gaseous sterilization agent essentially centered, in the transport direction, in the opening of said at least a number of the said separation means.

15. A method according to claim 13, further comprising introducing the gaseous sterilization agent in an upper portion of the gassing zone and evacuating the gaseous sterilization agent from the gassing zone in a lower portion thereof.

16. A method according to claim 13, further comprising intermittently transporting the packages in such a way that each of the packages is essentially centered, in the transport direction, in the opening of said respective one of the separation means in a gassing step where gaseous sterilization agent is injected into the packages.

17. A device for sterilizing packages with a gaseous sterilization agent comprising:
- a conveyor configured to convey the packages along a transport direction;
- a gassing chamber divided into a plurality of sub gassing zones by a plurality of partitions, the partitions being arranged along the transport direction;
- each partition including an opening sized to permit the packages to pass through the partition; and
- a plurality of inlets configured to introduce the gaseous sterilization agent into the gassing chamber, each of the inlets being aligned along the transport direction with a respective one of the partitions so that each of the inlets overlaps a respective one of the partitions when viewed along a direction orthogonal to the transport direction.

* * * * *